(12) United States Patent
Hawes et al.

(10) Patent No.: US 10,687,554 B2
(45) Date of Patent: Jun. 23, 2020

(54) CONNECTION DEVICE, CARTRIDGE AND ELECTRONIC VAPING DEVICE

(71) Applicants: Eric Hawes, Richmond, VA (US); Raymond Lau, Richmond, VA (US); Niall Gallagher, Richmond, VA (US)

(72) Inventors: Eric Hawes, Richmond, VA (US); Raymond Lau, Richmond, VA (US); Niall Gallagher, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 286 days.

(21) Appl. No.: 15/136,029

(22) Filed: Apr. 22, 2016

(65) Prior Publication Data

US 2016/0309788 A1 Oct. 27, 2016

Related U.S. Application Data

(60) Provisional application No. 62/151,160, filed on Apr. 22, 2015, provisional application No. 62/151,179, filed on Apr. 22, 2015.

(51) Int. Cl.
*A24F 47/00* (2020.01)
*A61M 15/00* (2006.01)
(Continued)

(52) U.S. Cl.
CPC ......... *A24F 47/008* (2013.01); *A61M 11/042* (2014.02); *A61M 15/0065* (2013.01);
(Continued)

(58) Field of Classification Search
CPC ... A24F 47/008; A61M 11/042; A61M 15/06; A61M 2205/15; A61M 2205/60; A61M 2205/276
(Continued)

(56) References Cited

U.S. PATENT DOCUMENTS 4,947,874 A * 8/1990 Brooks ................. A24F 47/008
128/202.21
5,666,977 A 9/1997 Higgins et al.
(Continued)

FOREIGN PATENT DOCUMENTS

GB 2502164 A 11/2013
WO WO-2014060267 A2 4/2014
(Continued)

OTHER PUBLICATIONS

Smokio, http://www.premiumlifestyle.co.uk/products/smokio-smart-wireless-e-cigarette, 2014.
(Continued)

*Primary Examiner* — Tu B Hoang
*Assistant Examiner* — Erin E McGrath
(74) *Attorney, Agent, or Firm* — Harness, Dickey & Pierce, P.L.C.

(57) ABSTRACT

At least one example embodiment discloses a cartridge for an electronic vapor (e-vapor) apparatus. The cartridge includes a pre-vapor formulation compartment configured to hold a solution therein and a first connector element configured to connect the cartridge to a power section of the e-vapor apparatus. The first connector element includes a processing device configured to communicate with the power section.

16 Claims, 13 Drawing Sheets

(51) Int. Cl.
  *A61M 15/06* (2006.01)
  *A61M 11/04* (2006.01)
(52) U.S. Cl.
  CPC ....... *A61M 15/06* (2013.01); *A61M 2205/276* (2013.01); *A61M 2205/3334* (2013.01); *A61M 2205/60* (2013.01)
(58) Field of Classification Search
  USPC .......................... 131/329; 392/386, 390, 404
  See application file for complete search history.

(56) References Cited

U.S. PATENT DOCUMENTS

| | | | |
|---|---|---|---|
| 7,699,052 | B2 | 4/2010 | Schiewe et al. |
| 2005/0016550 | A1 | 1/2005 | Katase |
| 2009/0266358 | A1 | 10/2009 | Sacristan Rock et al. |
| 2011/0011396 | A1* | 1/2011 | Fang ................... A24F 47/008 128/202.21 |
| 2011/0265806 | A1 | 11/2011 | Alarcon et al. |
| 2012/0174914 | A1 | 7/2012 | Pirshafiey et al. |
| 2012/0199663 | A1* | 8/2012 | Qiu ..................... A61M 11/041 239/8 |
| 2013/0087160 | A1 | 4/2013 | Gherghe |
| 2013/0182360 | A1 | 7/2013 | Stevens et al. |
| 2013/0220315 | A1* | 8/2013 | Conley ................ A24F 47/008 128/202.21 |
| 2013/0284192 | A1 | 10/2013 | Peleg et al. |
| 2013/0327327 | A1 | 12/2013 | Edwards et al. |
| 2013/0340775 | A1 | 12/2013 | Juster et al. |
| 2014/0007891 | A1 | 1/2014 | Liu |
| 2014/0096781 | A1 | 4/2014 | Sears et al. |
| 2014/0096782 | A1* | 4/2014 | Ampolini ............. A24F 47/008 131/328 |
| 2014/0107815 | A1 | 4/2014 | LaMothe |
| 2014/0123989 | A1 | 5/2014 | LaMothe |
| 2014/0157583 | A1 | 6/2014 | Ward et al. |
| 2014/0174459 | A1 | 6/2014 | Burstyn |
| 2014/0190830 | A1 | 7/2014 | Sturmer et al. |
| 2014/0224267 | A1 | 8/2014 | Levitz et al. |
| 2014/0246035 | A1 | 9/2014 | Minskoff et al. |
| 2014/0253144 | A1 | 9/2014 | Novak, III et al. |
| 2014/0261408 | A1 | 9/2014 | DePiano et al. |
| 2014/0261495 | A1 | 9/2014 | Novak, III et al. |
| 2014/0270727 | A1 | 9/2014 | Ampolini et al. |
| 2014/0270730 | A1 | 9/2014 | DePiano et al. |
| 2014/0299137 | A1 | 10/2014 | Kieckbusch et al. |
| 2014/0338685 | A1 | 11/2014 | Amir |
| 2014/0378790 | A1 | 12/2014 | Cohen |
| 2015/0059786 | A1* | 3/2015 | Li ....................... H01M 10/425 131/329 |
| 2015/0101625 | A1* | 4/2015 | Newton ............... H05B 1/0244 131/329 |
| 2015/0136158 | A1* | 5/2015 | Stevens ................ A24F 47/008 131/329 |

FOREIGN PATENT DOCUMENTS

| | | |
|---|---|---|
| WO | WO-2014060269 A1 | 4/2014 |
| WO | WO-2014/066730 A1 | 5/2014 |
| WO | WO-2014/095737 A1 | 6/2014 |
| WO | WO-2014125483 A1 | 8/2014 |
| WO | WO-2014-144678 A2 | 9/2014 |

OTHER PUBLICATIONS

Go Electronic Cigarette, "Igo 4Electronic Cigarette," http://www.electronic-cigarette.ie/Charger-iGO4, Feb. 19, 2015.

* cited by examiner

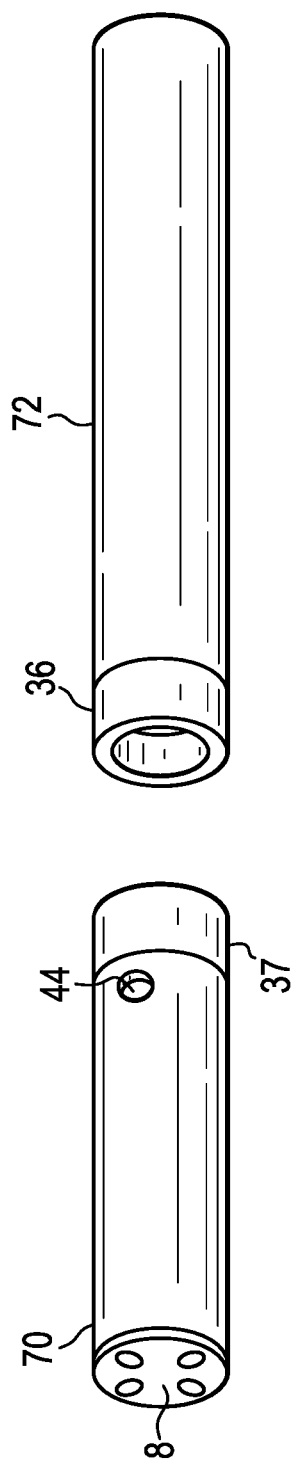

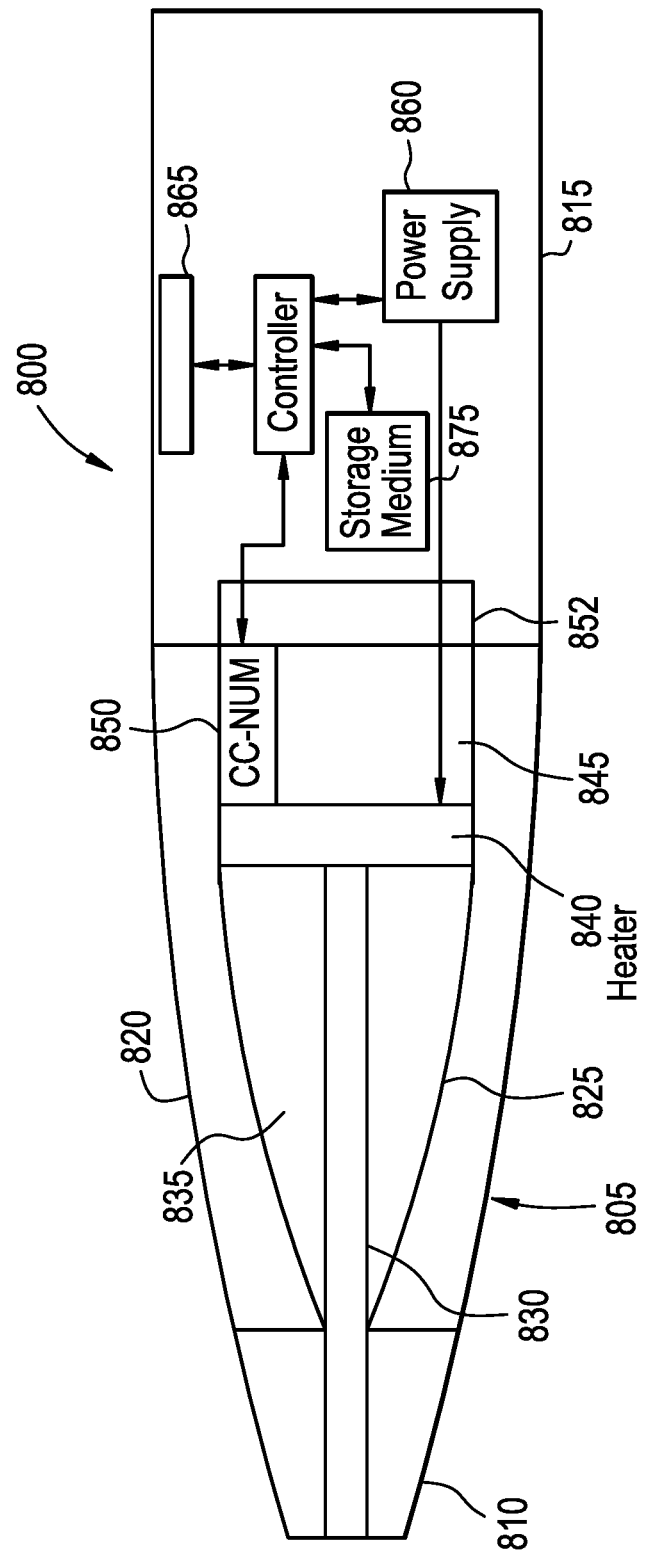

CONNECTION DEVICE, CARTRIDGE AND ELECTRONIC VAPING DEVICE

PRIORITY

This non-provisional patent application claims priority under § 119(e) to provisional U.S. application Nos. 62/151,160 filed on Apr. 22, 2015 and 62/151,179 filed on Apr. 22, 2015, both in the United States Patent and Trademark Office, the entire contents of each of which are incorporated herein by reference.

BACKGROUND

Field

At least some example embodiments relate generally to an e-vaping device.

Related Art

Electronic vaping devices are used to vaporize a pre-vapor formulation material into a vapor. These electronic vaping devices may be referred to as e-vaping devices. E-vaping devices include a heater which vaporizes a pre-vapor formulation to produce a vapor. An e-vaping device may include several e-vaping elements including a power source, a cartridge or e-vaping tank including the heater and along with a reservoir capable of holding the pre-vapor formulation.

SUMMARY

At least some example embodiments relate to an e-vaping device.

At least one example embodiment discloses a cartridge for an electronic vapor (e-vapor) apparatus. The cartridge includes a pre-vapor formulation compartment configured to hold a pre-vapor formulation therein and a first connector element configured to connect the cartridge to a power section of the e-vapor apparatus, the first connector element including a processing device configured to communicate with the power section.

In an example embodiment, the cartridge further includes at least one power connector configured to connect to the power section, the power connector being coupled to the processing device.

In an example embodiment, the processing device is under the at least one power connector.

In an example embodiment, the first connector element includes a first portion and a second portion divided by an indented portion of the first connector, the indented portion defining an opening between the first portion and the second portion, the at least one power connector extends from the first portion to the second portion, and the processing device is coupled to the at least one power connector in the first portion.

In an example embodiment, the at least one power connector includes two pronged elements and the processing device is in contact with a single prong element of the two pronged elements.

In an example embodiment, the processing device is not connected to a printed circuit board (PCB).

In an example embodiment, the processing device is a cryptographic coprocessor with non-volatile memory (CC-NVM).

In an example embodiment, the CC-NVM is configured to adjust cryptographic keys based on vaping parameters.

In an example embodiment, the processing device is on an exposed surface of the first connector element.

At least one example embodiment discloses an electronic vapor (e-vapor) apparatus including a first section including a controller and a second section including a pre-vapor formulation compartment configured to hold a pre-vapor formulation therein and a first connector element configured to connect the cartridge to the first section, the first connector element including a processing device configured to communicate with the controller.

In an example embodiment, the second section further includes at least one power connector configured to connect to a power supply of the first section.

In an example embodiment, the processing device is under the at least one power connector.

In an example embodiment, the first connector element includes a first portion and a second portion divided by an indented portion of the first connector, the indented portion defining an opening between the first portion and the second portion, the at least one power connector extends from the first portion to the second portion, and the processing device is coupled to the at least one power connector in the first portion.

In an example embodiment, the at least one power connector includes two pronged elements and the processing device is in contact with a single prong element of the two pronged elements.

In an example embodiment, the processing device is not connected to a printed circuit board (PCB).

In an example embodiment, the processing device is a cryptographic coprocessor with non-volatile memory (CC-NVM).

In an example embodiment, the CC-NVM is configured to adjust cryptographic keys based on vaping parameters.

In an example embodiment, the processing device is on an exposed surface of the first connector element.

BRIEF DESCRIPTION OF THE DRAWINGS

The above and other features and advantages of example embodiments will become more apparent by describing, example embodiments in detail with reference to the attached drawings. The accompanying drawings are intended to depict example embodiments and should not be interpreted to limit the intended scope of the claims. The accompanying drawings are not to be considered as drawn to scale unless explicitly noted.

FIG. 3A is a perspective view of the e-vaping device of FIG. 1, but with first and second sections separated from each other, according to an example embodiment;

FIG. 8 illustrates another example embodiment of an e-vaping device configured to utilize a connection arrangement shown in FIGS. 3B-C.

DETAILED DESCRIPTION

Figure 1:
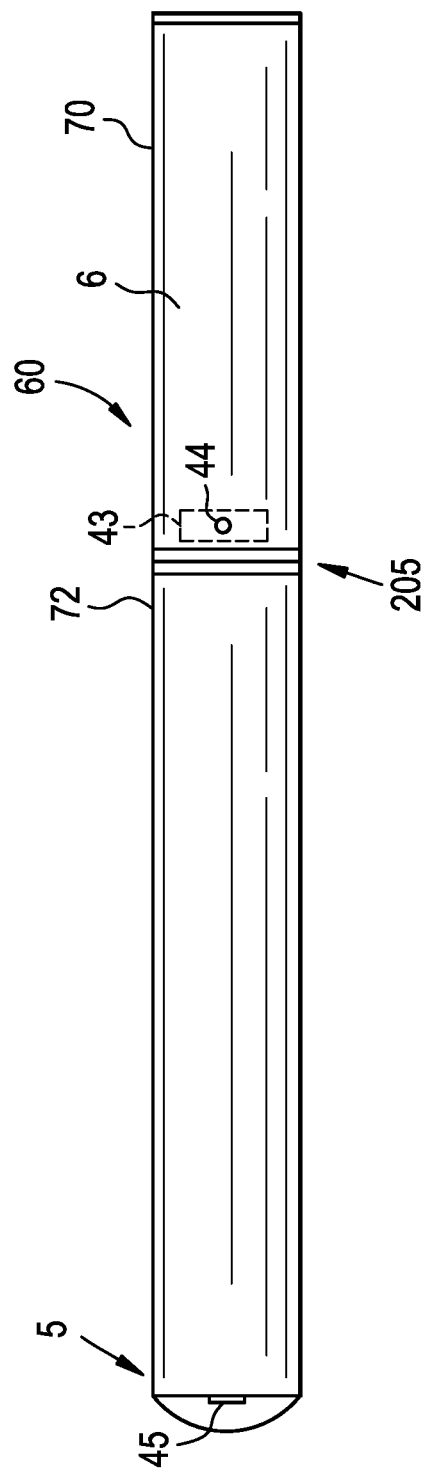
FIG. 1 is a view of an e-vaping device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments to cover all modifications, equivalents, and alternatives falling within the scope of example embodiments. Like numbers refer to like elements throughout the description, of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clea indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 2:
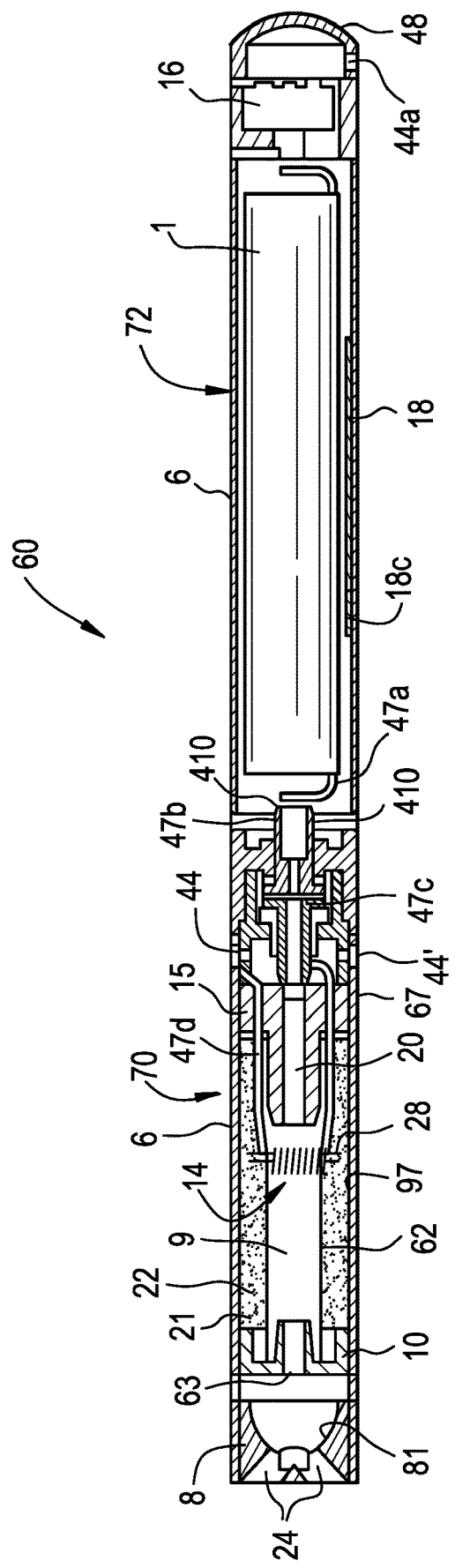
FIG. 2 is a side cross-sectional view of the e-vaping device shown in FIG. 1 and including a connector according to an example embodiment.

Referring to FIGS. 1-2, an electronic vaping (e-vaping) article 60 includes a replaceable cartridge (or first section) 70 and a reusable fixture (or second section) 72. The first section 70 and the second section 72 may be coupled together at a connection 205. The second section 72 may include a puff sensor 16 responsive to air drawn into the second section 72, a power supply 1 and a controller 18 configured to control integrally the puff sensor 16. However, the position of the controller 18 is not limited thereto. While the controller 18 is illustrated as being in a longitudinal position, it should be understood that the location of controller 18 is not limited thereto.

The controller 18 may utilize encryption to authenticate the first section 70. As will be described, the controller 18 communicates with a cryptographic coprocessor non-volatile memory (CC-NVM) package in a first connector element of the first section to authenticate the first section 70.

The controller 18 may be hardware, firmware, hardware executing software or any combination thereof. When the controller 18 is hardware, such existing hardware may include one or more Central Processing Units (CPUs), digital signal processors (DSPs), application-specific-integrated-circuits (ASICs), field programmable gate arrays (FPGAs) computers or the like configured as special purpose machines to perform the functions of the controller 18. As stated above, CPUs, DSPs, ASICs and FPGAs may generally be referred to as processing devices.

In the event where the controller 18 is a processor executing software, the controller 18 is configured as a special purpose machine to execute the software, stored in a computer readable storage medium 18*a*, to perform the functions of the at least one of the controller.

As disclosed herein, the term "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

The term CC-NVM may refer to a hardware module(s) including a processor for encryption and related processing.

More specifically, the non-volatile memory is encoded during manufacture with product and other information for authentication. For example, the non-volatile memory may store information such as a stock keeping unit (SKU) of the pre-vapor formulation in the pre-vapor formulation supply reservoir 22, software patches for the e-vaping device 60, and information communicated by the controller 18 of the e-vaping device 60 such as product usage information. Product usage information may include a puff count, puffing durations, and pre-vapor formulation level remaining in the reservoir. Moreover, the non-volatile memory may retain the recorded information even when the first section 70 becomes disconnected from the second section 72.

A pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerine and propylene glycol.

The first section 70 includes a pre-vapor formulation supply reservoir 22 (including pre-vapor formulation and optionally a pre-vapor formulation storage medium 21), a wick 28 that wicks pre-vapor formulation from the pre-vapor formulation supply reservoir 22, and a heater element 14 that heats the pre-vapor formulation in the wick to form a vapor in a central air channel 20. While FIG. 2 illustrates a wick, it should be understood that example embodiments are not limited to vaping devices including a wick. Upon completing the connection 205, the power supply 1 is electrically connected with the heater element 14 of the first section 70 upon actuation of the puff sensor 16. Air is drawn primarily into the first section 70 through one or more air inlets 44. As will be described in further detail below, example embodiments are not limited to e-vaping devices using a puff sensor to activate the vaping. Rather, example embodiments are also applicable to e-vaping devices that utilize another means for activation, such as a push button or a capacitive button.

The e-vaping article 60 described herein can be disposable or reusable. For example, once the pre-vapor formulation of the cartridge is spent, only the first section 70 is replaced.

In some example embodiments, the e-vaping device 60 can be about 80 mm to about 110 mm long, preferably about 80 mm to about 100 mm long and about 7 mm to about 8 mm in diameter. For example, the e-vaping device 60 is about 84 mm long and has a diameter of about 7.8 mm.

The first section 70 includes an outer tube 6 (or housing) extending in a longitudinal direction and an inner tube 62 coaxially positioned within the outer tube or housing 6. The second section 72 can also include an outer tube 6 (or housing) extending in a longitudinal direction.

The e-vaping device 60 can also include a central air passage 20 defined in part by inner tube 62 and an upstream seal 15. Moreover, the e-vaping device 60 includes a pre-vapor formulation supply reservoir 22. The pre-vapor formulation supply comprises a pre-vapor formulation material and optionally a pre-vapor formulation storage medium 21 operable to store the pre-vapor formulation material therein. In an embodiment, the pre-vapor formulation supply reservoir 22 is contained in an outer annulus between the outer tube 6 and the inner b 62. The annulus is sealed at an upstream end by the seal 15 and by a pre-vapor formulation stopper 10 at a downstream end so as to prevent leakage of the pre-vapor formulation material from the pre-vapor formulation supply reservoir 22.

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, poiyetheretherketone (PEEK), ceramic, and polyethylene. In one embodiment, the material is light and non-brittle.

In an example embodiment, the heater 14 is also contained in the inner tube 62 downstream of and in spaced apart relation to the portion of central air passage 20 defined by the seal 15. The heater 14 can be in the form of a wire coil, a planar body, a ceramic body, a single wire, a cage of resistive wire or any other suitable form. A wick 28 is in communication with the pre-vapor formulation material in the pre-vapor formulation supply reservoir 22 and in communication with the heater 14 such that the wick 28 disposes pre-vapor formulation material in proximate relation to the heater 14. The wick 28 may be constructed of a fibrous and flexible material. The wick 28 may include at least one filament having a capacity to draw a pre-vapor formulation. For example, the wick 28 may comprise a bundle of filaments which may include glass (or ceramic) filaments.

In another example embodiment, a bundle comprising a group of windings of glass filaments, for example, three of such windings, all which arrangements are capable of drawing pre-vapor formulation via capillary action via interstitial spacing between the filaments.

The power supply 1 in the second section 72 may be operably connected to the heater 14 (as described below) to apply voltage across the heater 14. The e-vaping device 60 also includes at least one air inlet 44 operable to deliver air to the central air passage 20 and/or other portions of the inner tube 62.

The e-vaping device 60 further includes a mouth-end insert 8 having at least two off-axis, diverging outlets 24. The mouth-end insert 8 is in fluid communication with the central air passage 20 via the interior of inner tube 62 and a central passage 63, which extends through the stopper 10.

As shown in FIGS. 3A-6B, the connection 205 includes a first connector element 37 and a second connector element 36. As will be described with reference to FIGS. 4-6B, the first connector element 37 includes a cryptographic coprocessor with non-volatile memory (CC-NVM) to transfer and receive data to and from the controller 18.

The connection 205 may include one or more rubber (resilient) gaskets positioned about a battery contact 47*c* of the first section 70 and a battery contact 47*b* of the second section 72, which provide an electrical connection, extending through the connection 205. The rubber gaskets may be axially compressed when the first connector element 37 is inserted into the second connector element 36 so as to provide a tactile sensation (feedback) that signifies the connection 205 has been formed.

The e-vaping device 60 includes at least one air inlet 44 formed in the outer tube 6, preferably adjacent the connection 205. In an example embodiment, the air inlets 44, 44' are sized and configured such that the e-vaping device 60 has a resistance to draw (RTD) in the range of from about 60 mm $H_2O$ to about 150 mm $H_2O$, more preferably about 90 mm $H_2O$ to about 110 mm $H_2O$, most preferably about 100 mm $H_2O$ to about 130 mm $H_2O$. However, in other example embodiments (e.g., FIGS. 7A-8), a range of 40-150 mm $H_2O$ may be utilized.

In an example embodiment, the second section 72 includes an air inlet 45 at an upstream end 5 of the e-vaping device 60, which is sized just sufficient to assure proper operation of the puff sensor 16, located nearby. Drawing action upon a mouth-end insert 8 is communicated to the puff sensor through the central air channel provided in the battery contact 47c of the first section 70 and the battery contact 47b of the second section 72 and along space 13 between the battery 1 and the housing of the second section 72.

Figure 3B:
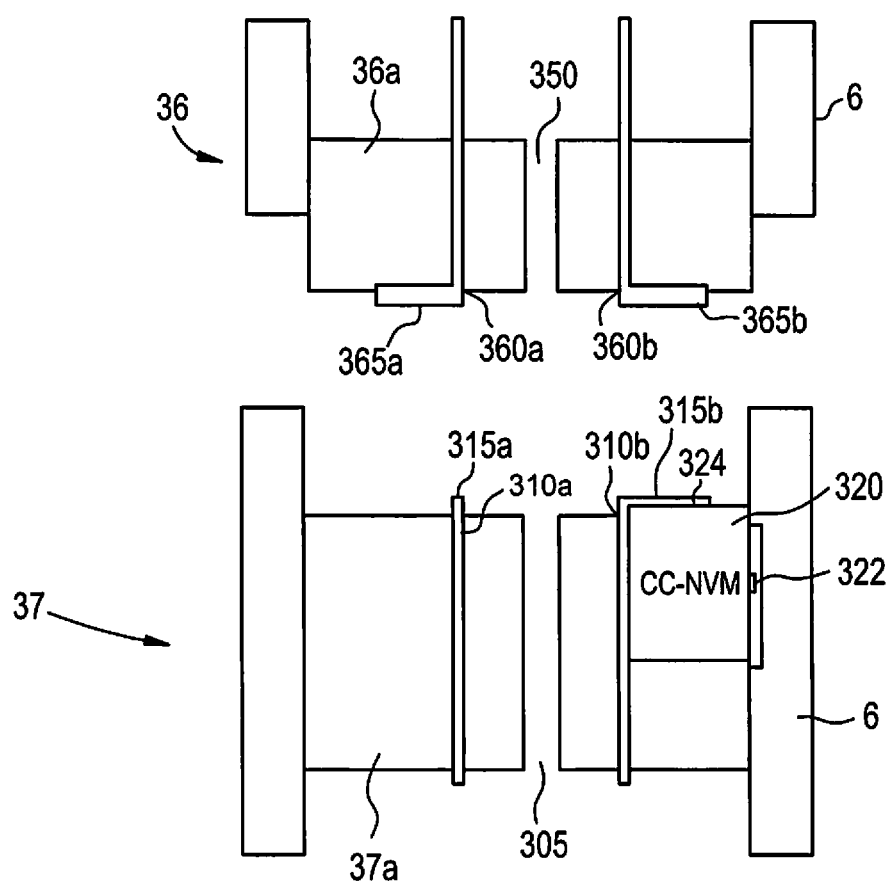
FIG. 3B illustrates a cross-sectional view of how the first and second sections may be connected, according to an example embodiment.

FIG. 3B illustrates a cross-sectional view of how the first and second sections may be connected, according to an example embodiment.

As shown in FIG. 3B, the first connector element 37 includes a connector piece 37a. The connector piece 37a has an interior surface that defines an air channel 305 through the connector piece 37a. Furthermore, the connector piece 37a includes slots 310a and 310b to receive battery contacts 315a and 315b, respectively.

Furthermore, the first connector element 37 includes a CC-NVM package 320. As will be described with reference to the example first connector elements below, the position of the CC-NVM package 320 is not limited to the position shown in FIG. 3B. The CC-NVM package 320 includes pins 322 and 324 to connect to the outer housing 6 and the battery contact 315b, respectively. Because the outer housing 6 is metal, the connection to the outer housing 6 provides a data communication line between the CC-NVM package 320 and the controller in the e-vaping device.

A pre-vapor formulation-tight seal(s) may be implemented between the pre-vapor formulation supply reservoir 22 and the first connector element 37 to prevent pre-vapor formulation from reaching the CC-NVM package 320 while allowing the battery contacts 315a and 315b to extend into the pre-vapor formulation supply reservoir 22 and connect with the heater 14.

The second connector element 36 is configured to mate with the first connector element 37. For example, the second connector element 36 may be designed such that the second connector element 36 provides a pre-vapor formulation-tight seal with one of the first connector elements shown in FIGS. 4-6A.

The second connector element 36 includes a connector piece 36a. The connector piece 36a has an interior surface that defines an air channel 350 through the connector piece 36a. Furthermore, the connector piece 36a includes slots 360a and 360b to receive battery contacts 365a and 365b, respectively.

The connection allows air to pass through the channels 305 and 350 and the battery contacts 315a and 315b to connect with the battery contacts 365a and 365b, respectively. The battery contacts 315a and 315b provided power to a heating element (e.g., the heater 14) and the battery contacts 365a and 365b are connected to a power supply (e.g., the power supply 1).

Since air flows through the channels 305 and 350, the connection shown in FIG. 3B may be used in e-vaping devices having a puff sensor. For example, FIG. 3D illustrates the connector elements 37 and 36 being connected at the connection 205.

Figure 3C:
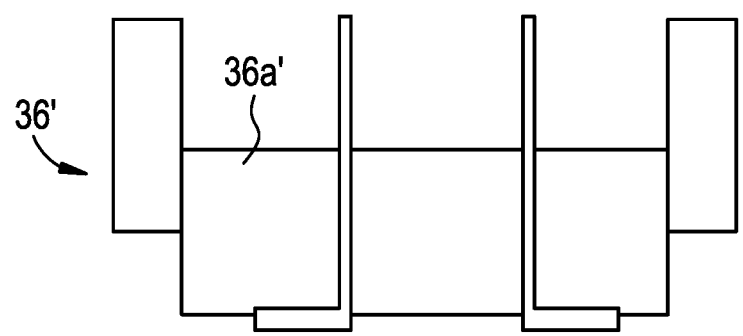
FIG. 3C illustrates another cross-section view of how the first and second sections may be connected, according to an example embodiment.
Figure 3C:
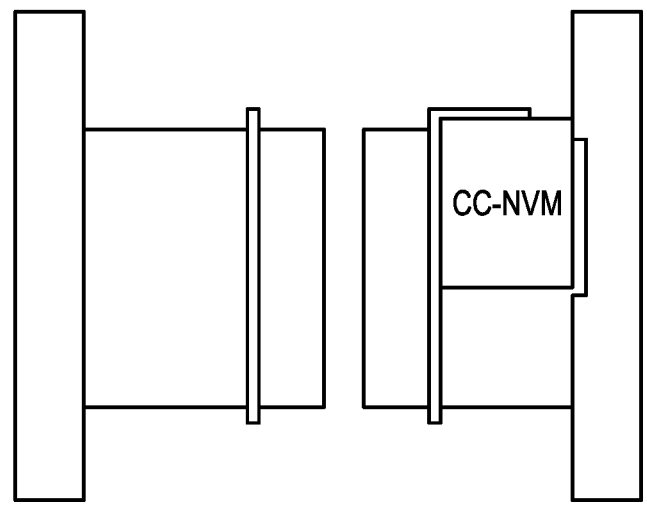
Figure 3D:
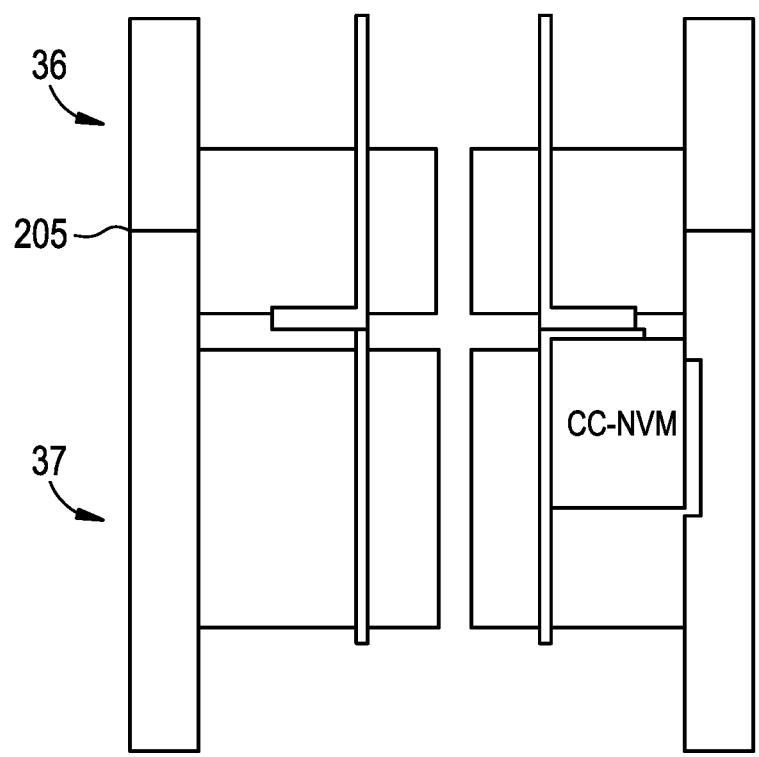
FIG. 3D illustrates a cross-section view of a connection shown the first and second sections shown in FIG. 3B.

FIG. 3C illustrates a cross-sectional view of how the first and second sections may be connected, according to an example embodiment.

Figure 3E:
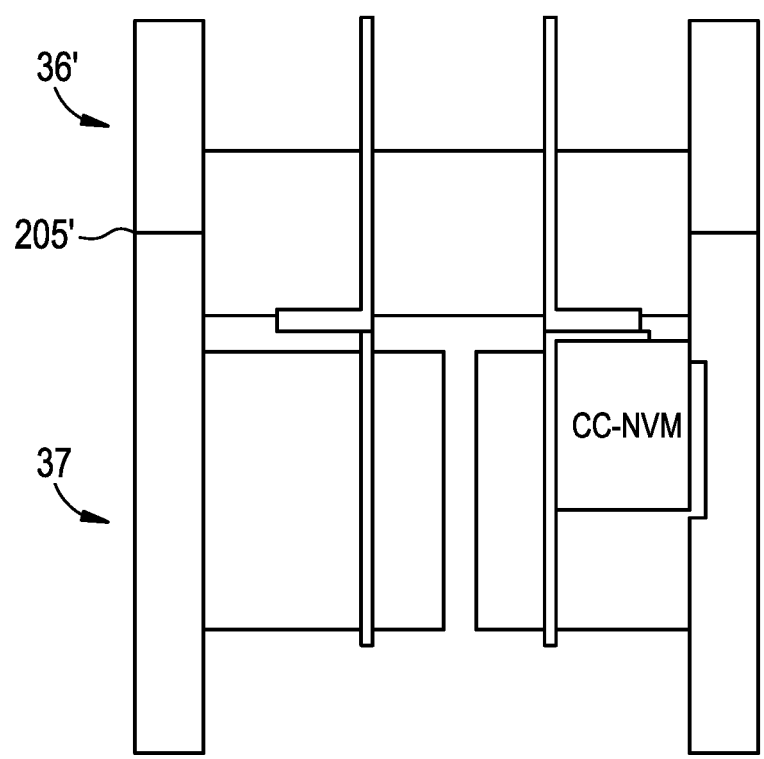
FIG. 3E illustrates a cross-section view of a connection shown the first and second sections shown in FIG. 3C.

In FIG. 3C, a second connector element 36' is the same as the second connector element 36 except a connector piece 36a' does not include an air channel. Thus, the example embodiment shown in FIG. 3C may be utilized in e-vaping devices that do not use a puff sensor, such as pod-type e-vaping devices (e.g., shown in FIGS. 7A-8B). FIG. 3e illustrates the connector elements 37 and 36' being connected at a connection 205'.

FIGS. 4-6B illustrate example embodiments of the first connector element shown in FIG. 3A. It should be understood that the dimensions of the first connector element according to example embodiments may be flexible and can be scaled to fit different e-vaping devices. Furthermore, the connector pieces do not have to have a circular cross section.

Figure 4:
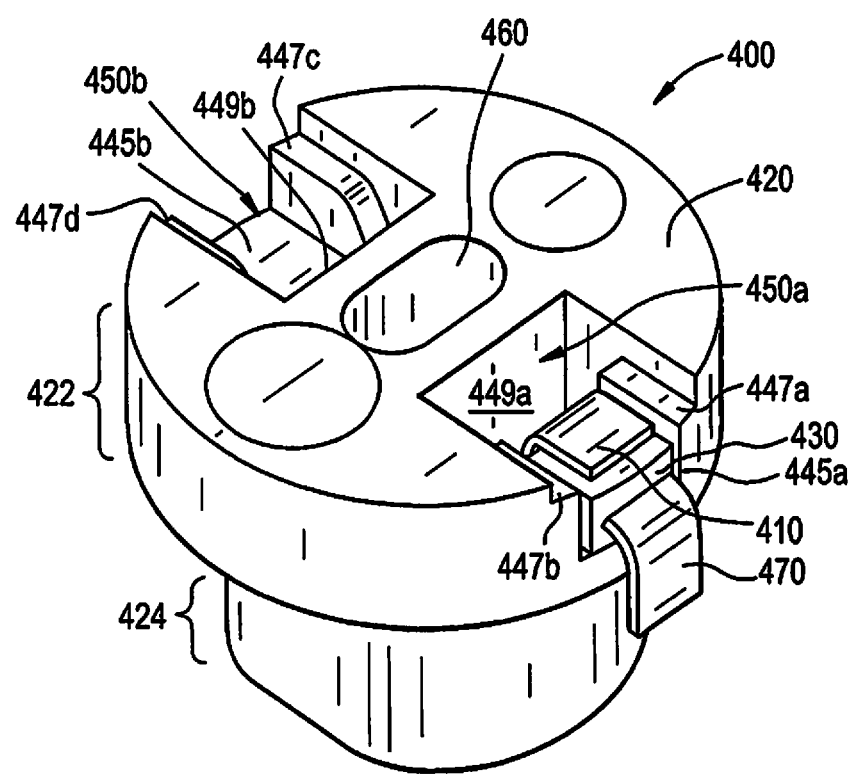
FIG. 4 illustrates an example embodiment of a first connector element shown in FIG. 3A.

As shown in FIG. 4, a first connector element 400 includes battery contacts (also referred to as power connectors) 410 and a cryptographic coprocessor with non-volatile memory (CC-NVM) package 430 in a connector piece 420. The CC-NVM package 430 may also be referred to as a processing device. Thus, while example embodiments are described with reference to a CC-NVM, it should be understood that other processing devices may be used for authentication and conveying information to the controller 18.

The connector piece 420 includes two slots 445a and 445b fitted to receive the CC-NVM package 430 and the battery contacts 410. For the sake of illustration purposes, only one of the battery contacts is illustrated.

The connector piece 420 includes a top portion 422 (portion nearest the section 72 when connected to the section 72) and a bottom portion 424. The top portion 422 is a cylindrically shaped and includes two opposing slots 445a and 445b fitted to receive the CC-NVM package 430 and the battery contacts 410.

As shown, the CC-NVM package 430 does not utilize a printed circuit board (PCB). The CC-NVM package 430 may be friction fit into the slot 445a. As a result, a size and cost of the section 70 is reduced.

Moreover, the CC-NVM package 430 may include at least one pin 470 and utilizes the pin 470 to contact with the outer housing 6 shell. The CC-NVM package 430 utilizes the outer housing 6 as a data communication line to communicate with the controller 18. Another pin connects the CC-NVM package 430 to the battery contact 410.

The slot 445a is defined by elevated portions 447a, 447b and a back end 449a of a groove 450a. Similarly, the slot 445b is defined by elevated portions 447c, 447d and a back end 449b of a groove 450b. The grooves 450a and 450b oppose each other.

The CC-NVM package 430 may work with an encryption system in the e-vapor device 60 to authenticate the first section 70. More specifically, the non-volatile memory of the CC-NVM package 430 is encoded during manufacture with product and other information for authentication. For example, the non-volatile memory of the CC-NVM package 430 may store information regarding the chemical composition of the pre-vapor formulation in the pre-vapor formulation supply reservoir 22, software patches for the e-vaping device 60, a puff count, puffing duration, pre-vapor formulation level and puff parameters. Moreover, the non-volatile memory of the CC-NVM package 430 may record information communicated by the controller 18 of the e-vaping device 60.

In an example embodiment, the CC-NVM package 430 may be a programmable read-only memory (PROM), for example. The CC-NVM may transfer updates, such as power control, to the controller 18 and information such as a blacklist (e.g., a list of prohibited items such as counterfeit pods and cartridges), marketing and promotional materials to the controller 18.

The first connector element 400 may be referred to as a contact top mount connector because the battery contacts as well as the CC-NVM package 430 are exposed at the top portion 422 of the connector piece 420.

The bottom portion 424 is cylindrically shaped and has a length greater than the top portion 422 and a diameter less than the top portion 422.

Furthermore, the connector piece 420 defines a channel 460 through the connector piece 420 to allow air to pass through the connector piece 420. While the channel 460 is illustrated as a central air channel, example embodiments are not limited thereto. For example, the connector piece 420 may have side air channel. Moreover, the CC-NVM package 430 may be made to fit around the connector piece 420.

The connector piece 420 may be made of hard plastic that can be molded. The materials of the connector piece 420 may have some capacity to be flexible to facilitate friction fitting of parts. Also, the materials should not chemically react in a deleterious way with the flavor ingredients or other ingredients of pre-vapor formulations.

Figure 5A:
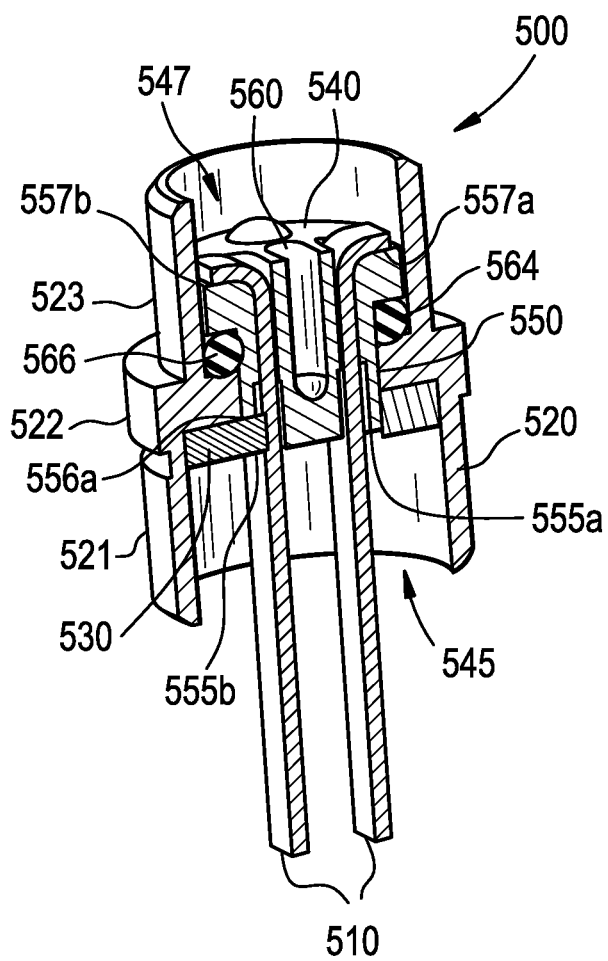
FIG. 5A illustrates a cross-section view of a first connector element according to an example embodiment.
Figure 5B:
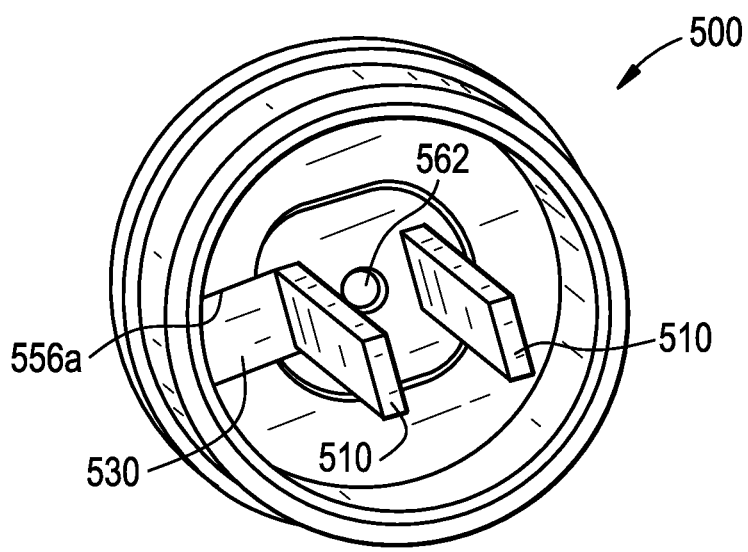
FIG. 5B illustrates a bottom view of the first connector element of FIG. 5A.

FIGS. 5A-5B illustrate an example embodiment of the first connector element shown in FIG. 3A.

FIG. 5A illustrates a cross-section view of a first connector element 500. FIG. 5B illustrates a bottom view of the first connector element 500.

The first connector element 500 includes a connector piece 520, a CC-NVM package 530, a gasket 540 and battery contacts 510 protruding through the gasket 540. The gasket 540 may be made of hard plastic that can be molded. The CC-NVM package 530 may be the same as the CC-NVM package 430 or at least configured to perform the same functions as the CC-NVM package 430.

The connector piece 520 includes a first portion 521, an intermediate portion 522 and a second portion 523. The connector piece 520 may be made of metal and may be part of the outer housing 6 or connected to the outer housing 6. Thus, the connector piece 520 may provide a data connection for the CC-NVM package 530 to the controller in the e-vaping device because a pin of the CC-NVM package 530 is connected to the connector piece 520.

An inside surface area of the first portion 521 defines a channel 545 and an inside surface area of the second portion 523 defines a channel 547. The intermediate portion 522 defines an opening 550 between the first portion 521 and the second portion 523 thereby connecting the channels 545 and 547. A diameter of the channel 545 is larger than a diameter of the channel 547. A diameter of the opening is less than the diameters of the channels 545 and 547.

The gasket 540 extends from the channel 547 through the opening 550 and into the channel 545. The gasket 540 includes two slots 555a and 555b that extend through the gasket and hold the battery contacts 510. The gasket 540 further includes indented notches 557a, 557b at ends of the slots 555a and 555, respectively. The notches 557a, 557b are fitted to receive ends of the battery contacts 510.

The gasket 540 further includes an internal surface 560 that defines a channel 562 through the gasket to allow air to flow between the channels 545 and 547.

A seal 564 provides a substantially pre-vapor formulation-tight seal with an interior surface 566 of the connector piece 520. The seal 564 may be made of a plastic.

As shown in FIGS. 5A-5B, the CC-WM package 530 is connected to one of the battery contacts 510 and may be connected to the connector piece 520. The gasket 540 includes a notch 556a on one side to allow the CC-NVM package 530 to contact one of the battery contacts. Because the gasket 540 includes the notch 556a, a portion of the gasket 540 extends into the channel 547 whereas the portion of the gasket 540 with the notch 556a ends at where the first portion 521 and intermediate portion 522 meet.

Figure 6B:
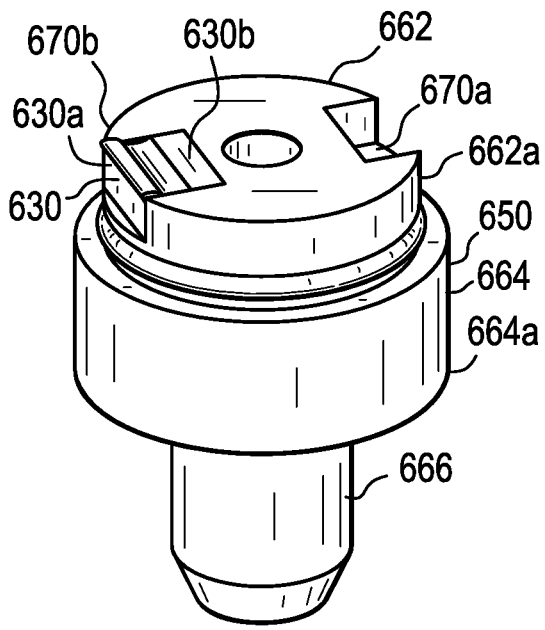
FIG. 6B illustrates an example embodiment of a gasket in the first connector element of FIG. 6A.
Figure 6A:
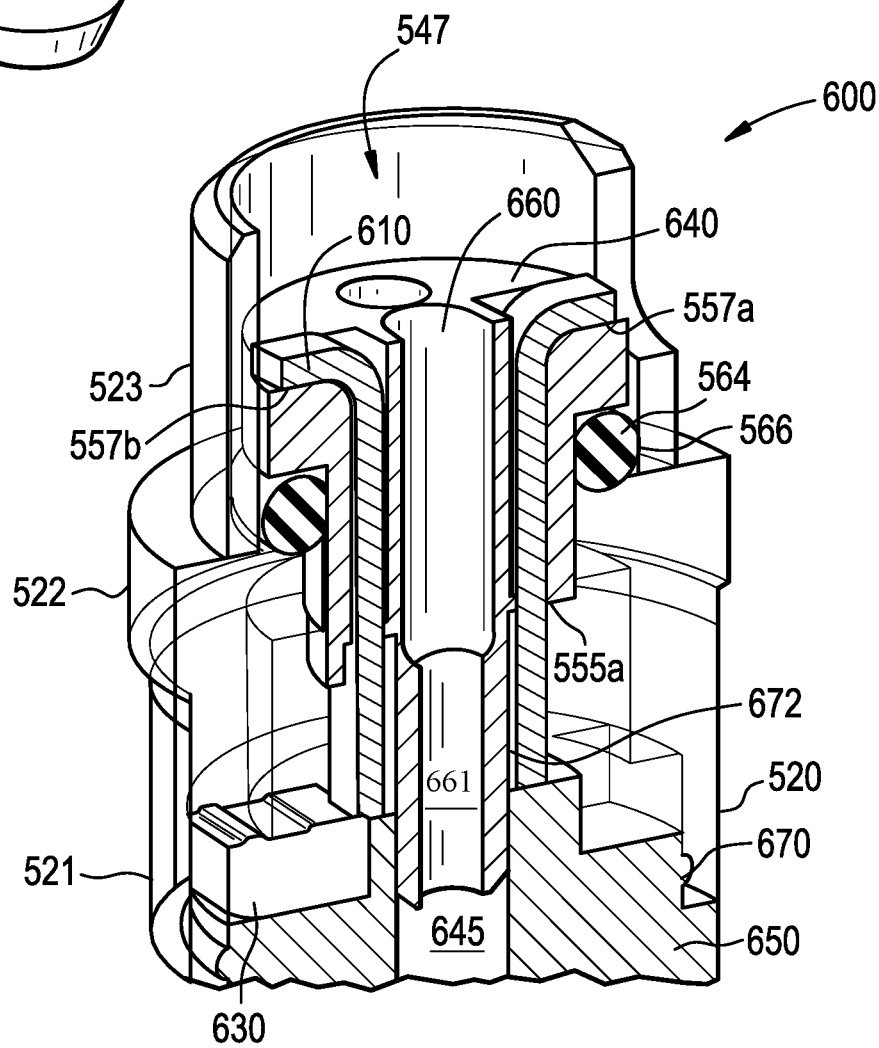
FIG. 6A illustrates an example embodiment of the first connector element shown in FIG. 3A.

FIG. 6A illustrates an example embodiment of the first connector element shown in FIG. 3A. FIG. 6B illustrates an example embodiment of a gasket in the first connector element of FIG. 6A.

As shown in FIG. 6A, a first connector element 600 includes the connector piece 520, a CC-NVM package 630, a first gasket 640, a second gasket 650 and battery contacts 610 protruding through the first gasket 640. The CC-NVM package 630 may be the same as the CC-NVM package 530 or at least configured to perform the same functions as the CC-NVM package 530.

The connector element 600 may be referred to as an in-gasket flat contact connector because the CC-NVM package 630 is in a flat position in the second gasket 650 and contacts one of the battery contacts 610 such that the connection is substantially normal. The CC-NVM package 630 is connected to the battery contact 610 to receive power.

The connector piece 520 may provide a data connection for the CC-NVM package 630 to the controller in the e-vaping device because a pin 630a of the CC-NVM package 630 is connected to the connector piece 520. A pin 630b may connect to the battery contact 610 to receive power.

The first gasket 640 is the same as the gasket 540 except an internal surface 660 is longer in a longitudinal direction that the internal surface 560 and the first gasket 640 does not include a notch to receive the CC-NVM package 630. The internal surface 660 defines a channel 661 through the first gasket 640 to allow air to flow between the channel 547 and a channel 645 defined by an inner surface 655 of the second gasket 650. The first gasket 640 further includes an extended portion 672 that extends into the channel 645.

As shown in FIG. 6B, second gasket 650 includes a top portion 662, an intermediate portion 664 and a bottom portion 666. The top portion. 662 is a cylindrically shaped and includes two opposing grooves 670a and 670b fitted to receive the CC-NVM package 630.

The second gasket 650 may be made of hard plastic that can be molded. The materials of the second gasket 650 may have some capacity to be flexible to facilitate friction fitting of parts. Also, the materials should be relatively inert and not chemically react in a deleterious way with the flavor ingredients or other ingredients of pre-vapor formulations.

A diameter of an outer surface 664a of the intermediate portion 664 is larger than a diameter of an outer surface 662a of the top portion. 662. The outer surface 664a provides a substantially pre-vapor formulation-tight seal with an interior surface 670 of the connector piece 520.

As shown in FIG. 6A, the CC-NVM package 630 does not utilize a printed circuit board (PCB). As a result, a size and cost of the section 70 is reduced.

Moreover, as described and shown with reference to FIGS. 4-6B, a CC-NVM package may be housed in different locations of a first connector element. In FIG. 4, the CC-NVM package 430 is embedded at one side of a gasket/connector, in FIGS. 5A-5B, the CC-NVM package 530 is embedded as part of a ring that fits around a gasket/connector; and in FIG. 6A, the CC-NVM package 630 is embedded in a connector separated from another connector.

In an embodiment, a heater 14 is also contained in the inner tube 62 downstream of and in spaced apart relation to the portion of central air passage 20 defined by the seal 15. The heater 14 can be in the form of a wire coil, a planar body, a ceramic body, a single wire, a cage of resistive wire or any other suitable form. A wick 28 is in communication with the pre-vapor formulation material in the pre-vapor formulation supply reservoir 22 and in communication with the heater 14 such that the wick 28 disposes pre-vapor formulation material in proximate relation to the heater 14. The wick 28 may be constructed of a fibrous and flexible material. The wick 28 may include at least one filament having a capacity to draw a pre-vapor formulation. For example, the wick 28 may comprise a bundle of filaments which may include glass (or ceramic) filaments. In another embodiment, a bundle comprising a group of windings of glass filaments, for example, three of such windings, all which arrangements are capable of drawing pre-vapor formulation via capillary action via interstitial spacing between the filaments.

A power supply 1 in the second section 72 may be operably connected to the heater 14 (as described below) to apply voltage across the heater 14. The e-vaping device 60 also includes at least one air inlet 44 operable to deliver air to the central air passage 20 and/or other portions of the inner tube 62.

The e-vaping device 60 further includes a mouth-end insert 8 having at least two off-axis, diverging outlets 24. The mouth-end insert 8 is in fluid communication with the central air passage 20 via the interior of inner tube 62 and a central passage 63, which extends through the stopper 10.

The wick 28, pre-vapor formulation supply reservoir 22 and mouth-end insert 8 are contained in the cartridge 70 and the power supply 1 is contained in the second section 72. In one embodiment, the first section (the cartridge) 70 is disposable and the second section (the fixture) 72 is reusable.

The sections 70, 72 can be attached by the first and second connector elements 37 and 36, as described above, whereby the downstream section 70 can be replaced when the pre-vapor formulation supply reservoir 22 is used up. Having a separate first section 70 and second section 72 provides a number of advantages. First, if the first section 70 contains the at least one heater 14, the pre-vapor formulation supply reservoir 22 and the wick 28, all elements which are potentially in contact with the pre-vapor formulation are disposed of when the first section. 70 is replaced. Thus, there will be no cross-contamination between different mouth-end inserts 8, for example, when using different pre-vapor formulation materials. Also, if the first section 70 is replaced at suitable intervals, there is little chance of the heater becoming clogged with pre-vapor formulation. Optionally, the first section 70 and the second section 72 are arranged to releasably lock together when engaged.

In one embodiment, the outer tube 6 can include a clear window formed of a transparent material so as to allow an adult vaper to see the amount of pre-vapor formulation material remaining in the pre-vapor formulation supply reservoir 22. The clear window can extend at least a portion of the length of the first section 70 and can extend fully or partially about the circumference of the first section 70. In another embodiment, the outer tube 6 can be at least partially formed of a transparent material so as to allow an adult vaper to see the amount of pre-vapor formulation material remaining in the pre-vapor formulation supply reservoir 22.

In an embodiment, the at least one air inlet 44 includes one or two air inlets 44, 44'. Alternatively, there may be three, four, five or more air inlets. If there is more than one air inlet 44, 44', the air inlets 44, 44' are located at different locations along the e-vaping device 60. For example, as shown in FIG. 2, an air inlet 44a can be positioned at the upstream end of the e-vaping device adjacent a puff sensor 16 such that the puff sensor 16 supplies power to the heater 14 upon sensing a negative pressure. Air inlet 44a should communicate with the mouth-end insert 8 so that a draw upon the mouth-end insert activates the puff sensor 16. The air from the air inlet 44a can then flow along the battery and to the central air passage 20 in the seal 15 and/or to other portions of the inner tube 62 and/or outer tube 6. At least one additional air inlet 44, 44' can be located adjacent and upstream of the seal 15 or at any other desirable location. Altering the size and number of air inlets 44, 44' can also aid in establishing the resistance to draw of the e-vaping device 60.

In an embodiment, the heater 14 is arranged to communicate with the wick 28 and to heat the pre-vapor formulation material contained in the wick 28 to a temperature sufficient to vaporize the pre-vapor formulation material and form a vapor.

The heater 14 may be a wire coil surrounding wick 28, a mesh, a surface or made out of a ceramic material for example. Examples of suitable electrically resistive materials include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and superalloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 14 comprises at least one material selected from the group consisting of stainless steel, copper, copper alloys, nickel-chromium alloys, superalloys and combinations thereof. In an embodiment, the heater 14 is formed of nickel-chromium alloys or iron-chromium alloys. In one embodiment, the heater 14 can be a ceramic heater having an electrically resistive layer on an outside surface thereof.

In another embodiment, the heater 14 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al). Use of iron-aluminides is particularly advantageous in that they exhibit high resistivity. FeAl exhibits a resistivity of approximately 180 micro-ohms, whereas stainless steel exhibits approximately 50 to 91 micro-ohms. The higher resistivity lowers current draw or load on the power supply (battery) 1.

In one embodiment, the heater 14 comprises a wire coil which at least partially surrounds the wick 28. In that embodiment, the wire may be a metal wire and/or the heater coil that extends partially along the length of the wick 28.

The heater coil may extend fully or partially around the circumference of the wick 28. In another embodiment, the heater coil is not in contact with the wick 28.

The heater 14 heats pre-vapor formulation in the wick 28 by thermal conduction. Alternatively, heat from the heater 14 may be conducted to the pre-vapor formulation by means of a heat conductive element or the heater 14 may transfer heat to the incoming ambient air that is drawn through the e-vaping device 60 during use, which in turn heats the pre-vapor formulation by convection.

In one embodiment, the wick comprises a ceramic material or ceramic fibers. As noted above, the wick 28 is at least partially surrounded by the heater 14. Moreover, in an embodiment, the wick 28 extends through opposed openings in the inner tube 62 such that end portions of the wick 28 are in contact with the pre-vapor formulation supply reservoir 22.

The wick 28 may comprise a plurality or bundle of filaments. In one embodiment, the filaments may be generally aligned in a direction transverse to the longitudinal direction of the e-vaping device, but the example embodiments are not limited to this orientation. In one embodiment, the structure of the wick 28 is formed of ceramic filaments capable of drawing pre-vapor formulation via capillary action via interstitial spacing between the filaments to the heater 14. The wick 28 can include filaments having a cross-section which is generally cross-shaped, clover-shaped, Y-shaped or in any other suitable shape.

The wick 28 includes any suitable material or combination of materials. Examples of suitable materials are glass filaments and ceramic or graphite based materials. Moreover, the wick 28 may have any suitable capillarity accommodate vapor generating pre-vapor formulations having different physical properties such as density, viscosity, surface tension and vapor pressure. The capillary properties of the wick 28, combined with the properties of the solution, ensure that the wick 28 is always wet in the area of the heater 14 to avoid overheating of the heater 14.

Instead of using a wick, the heater can be a porous material of sufficient capillarity and which incorporates a resistance heater formed of a material having a high electrical resistance capable of generating heat quickly.

In one embodiment, the wick 28 and the pre-vapor formulation storage medium 21 of the pre-vapor formulation supply reservoir 22 are constructed from an alumina ceramic. In another embodiment, the wick 28 includes glass fibers and the pre-vapor fbrmulation storage medium 21 includes a cellulosic material or polyethylene terephthalate.

In an embodiment, the power supply 1 includes a battery arranged in the e-vaping device 60 such that such that an anode 47a is downstream of a cathode. A battery contact 47b (e.g., battery contacts 410) contacts the downstream end of the power supply 1.

More specifically, a batter contact 47b (e.g., power connector) of the second section 72 preferably contacts the battery contact 47a. The outer housing 6 is formed of metal so as to complete the electrical circuit.

Electrical connection between the battery contact 47a of the power supply 1 and the heater 14 in the first section 70 is established through a battery contact 47b in the second section 72 of the e-vaping device 60 and a battery contact 47c of the cartridge 70 and an electrical lead 47d connecting a rim portion of the battery contact 47c with one end of the heater 14. The outer housing 6 can be formed of a metal so as to complete the electrical connection.

The battery contacts may be highly conductive and temperature resistant while a coiled section of the heater 14 is highly resistive so that heat generation occurs primarily along the coils of the heater 14.

The power supply 1 may be a Lithium-ion battery or one of its variants, for example a Lithium-ion polymer battery. Alternatively, the power supply 1 may be a Nickel-metal hydride battery, a Nickel cadmium battery, a Lithium-manganese battery, a Lithium-cobalt battery or a fuel cell. In that case, the e-vaping device 60 is usable until the energy in the power supply is depleted. Alternatively, the power supply 1 may be rechargeable and include circuitry allowing the battery to be chargeable by an external charging device. In that case, the circuitry, when charged, provides power for a desired (or alternatively a pre-determined) puff count, after which the circuitry must be re-connected to an external charging device. The controller 18 controls the control circuitry.

The controller 18 is configured to communicate with the CC-NVM package 430, 530 or 630 to authenticate the section 70.

The puff sensor 16 is operable to sense an air pressure drop and initiate application of voltage from the power supply 1 to the heater 14. The CC-NVM packages 430, 530 or 630 may use puff parameters (e.g., puff duration) to strengthen cryptographic keys by leveraging the random nature of the parameters. For example, encryption algorithms rely on the use of random numbers. The security of these algorithm depends on how truly random these numbers are. These numbers are usually pre-generated and coded into the processor or memory devices. Example embodiments increase the randomness of the numbers used for the encryption by using the puffing parameters e.g. puff durations, intervals between puffs, or combinations of them, to generate numbers that are more random and more varying from individual to individual than pre-generated random numbers.

The control circuitry can also include a heater activation light 48 operable to glow when the heater 14 is activated. In one embodiment, the heater activation light 48 comprises an LED and is at an upstream end of the e-vaping device 60 so that the heater activation light 48 takes on the appearance of a burning coal during a puff. Moreover, the heater activation light 48 can be arranged to be visible to the adult vaper. In addition, the heater activation light 48 can be utilized for e-vaping system diagnostics. The light 48 can also be configured such that the adult vaper can activate and/or deactivate the light 48 for privacy, such that the light 48 would not activate during \Taping if desired.

The at least one air inlet 44a is located adjacent the puff sensor 16, such that the puff sensor 16 senses air flow indicative of an adult vaper taking a puff and activates the power supply 1 and the heater activation light 48 to indicate that the heater 14 is working.

A control circuit is integrated with the puff sensor 16 and supplies power to the heater 14 responsive to the puff sensor 16, for example, with a maximum, time-period limiter.

Alternatively, the control circuitry may include a manually operable switch for an adult vaper to initiate the vaping. The time-period of the electric current supply to the heater may be pre-set depending on the amount of pre-vapor formulation desired to be vaporized. The control circuitry may be programmable for this purpose. Alternatively, the circuitry may supply power to the heater as long as the puff sensor detects a pressure drop.

When activated, the heater 14 heats a portion of the wick 28 surrounded by the heater for less than about 10 seconds, more preferably less than about 7 seconds. Thus, the power cycle (or maximum puff length) can range in period from about 2 seconds to about 10 seconds (e.g., about 3 seconds to about 9 seconds, about 4 seconds to about 8 seconds or about 5 seconds to about 7 seconds).

In an embodiment, the pre-vapor formulation supply reservoir 22 includes a pre-vapor formulation storage medium 21 containing a solution. In the embodiment shown in FIG. 2, the pre-vapor formulation supply reservoir 22 is contained in an outer annulus between inner tube 62 and outer tube 6 and between stopper 10 and the seal 15. Thus, the pre-vapor formulation supply reservoir 22 at least partially surrounds the central air passage 20 and the heater 14 and the wick 14 extend between portions of the pre-vapor formulation supply reservoir 22. The pre-vapor formulation storage material may be a fibrous material comprising cotton, polyethylene, polyester, rayon and combinations thereof. The fibers may have a diameter ranging in size from about 6 microns to about 15 microns (e.g., about 8 microns to about 12 microns or about 9 microns to about 11 microns). The pre-vapor formulation storage medium 21 may be a sintered, porous or foamed material. Also, the fibers may be sized to be irrespirable and can have a cross-section which has a y shape, cross shape, clover shape or any other suitable shape. In the alternative, the reservoir 22 may comprise a filled tank lacking a pre-vapor formulation storage medium 21.

Also, the pre-vapor formulation material has a boiling point suitable for use in the e-vaping device 60. If the boiling point is too high, the heater 14 will not be able to vaporize pre-vapor formulation in the wick 28. However, if the boiling point is too low, the pre-vapor formulation may vaporize without the heater 14 being activated.

The pre-vapor formulation material may include a tobacco-containing material including volatile tobacco flavor compounds which are released from the pre-vapor formulation upon heating. The pre-vapor formulation may also be a tobacco flavor containing material or a nicotine-containing material. Alternatively, or in addition, the pre-vapor formulation may include a non-tobacco material.

In use, pre-vapor formulation material is transferred from the pre-vapor formulation supply reservoir 22 and/or pre-vapor formulation storage medium 21 in proximity of the heater 14 by capillary action in the wick 28. In one embodiment, the wick 28 has a first end portion 29 and a second opposite end portion 31 as shown in FIG. 4. The first end portion 29 and the second end portion 31 extend into opposite sides of the pre-vapor formulation storage medium 21 for contact with pre-vapor formulation material contained therein. The heater 14 at least partially surrounds a central portion of the wick 28 such that when the heater 14 is activated, the pre-vapor formulation in the central portion of the wick 28 is vaporized by the heater 14 to vaporize the pre-vapor formulation material and form a vapor.

One advantage of an embodiment is that the pre-vapor formulation material in the pre-vapor formulation supply reservoir 22 is protected from oxygen (because oxygen cannot generally enter the pre-vapor formulation storage portion via the wick) so that the risk of degradation of the pre-vapor formulation material is significantly reduced. Moreover, in some embodiments in which the outer tube 6 is not clear, the pre-vapor formulation supply reservoir 22 is protected from light so that the risk of degradation of the pre-vapor formulation material is significantly reduced. Thus, a high level of shelf-life and cleanliness can be maintained.

Referring to FIG. 2, the mouth-end insert 8, includes at least two diverging outlets 24 (e.g., 3, 4, 5 or more). The outlets 24 of the mouth-end insert 8 are located at ends of off-axis passages and are angled outwardly in relation, to the longitudinal direction of the e-vaping device 60 (i.e., divergently). As used herein, the term "off-axis" denotes at an angle to the longitudinal direction of the e-vaping device. Also, the mouth-end insert (or flow guide) 8 may include outlets uniformly distributed around the mouth-end insert 8 so as to substantially uniformly distribute vapor during use. Thus, as the vapor passes into an adult vaper's mouth, the vapor enters the mouth and moves in different directions so as to provide a full mouth feel as compared to e-vaping devices having an on-axis single orifice which directs the vapor to a single location.

In addition, the outlets 24 and off-axis passages are arranged such that droplets of pre-vapor formulation material carried in the vapor impact interior surfaces 81 at the mouth-end insert 8 and/or interior surfaces of the off-axis passages such that the droplets are removed or broken apart. In an embodiment, the outlets of the mouth-end insert are located at the ends of the off-axis passages and are angled at 5 to 60 degrees with respect to the central axis of the outer tube 6 so as to more completely distribute vapor throughout a mouth of an adult vaper during use and to remove droplets.

Preferably, each outlet has a diameter of about 0.015 inch to about 0.090 inch (e.g., about 0.020 inch to about 0.040 inch or about 0.028 inch to about 0.038 inch). The size of the outlets 24 and off-axis passages 80 along with the number of outlets can be selected to adjust the resistance to draw (RTD) of the e-vaping device 60, if desired.

As shown in FIG. 2, an interior surface 81 of the mouth-end insert 8 can comprise a generally domed surface. Alternatively, as shown in FIG. 2B, the interior surface 81' of the mouth-end insert 8 can be generally cylindrical or frustoconical, with a planar end surface. The interior surface is substantially uniform over the surface thereof or symmetrical about the longitudinal axis of the mouth-end insert 8. However, in other embodiments, the interior surface can be irregular and/or have other shapes.

The mouth-end insert 8 is integrally affixed within the tube 6 of the cartridge. Moreover, the mouth-end insert 8 may be formed of a polymer selected from the group consisting of low density polyethylene, high density polyethylene, polypropylene, polyvinylchloride, polyetheretherketone (PEEK) and combinations thereof. The mouth-end insert 8 may also be colored if desired.

In an embodiment, the e-vaping device 60 also includes various embodiments of an air flow diverter or air flow diverter means. The air flow diverter is operable to manage air flow at or about around the heater so as to abate a tendency of drawn air to cool the heater, which could otherwise lead to diminished vapor output.

In one embodiment, the e-vaping device 60 can also include a filter segment upstream of the heater 14 and operable to restrict flow of air through the e-vaping device 60. The addition of a filter segment can aid in adjusting the resistance to draw.

In one embodiment, a wick 28 may be in communication with the interior of the pre-vapor formulation supply reservoir 22 and in communication with a heater 14 such that the wick 28 draws pre-vapor formulation via capillary action from the supply reservoir 22 into proximity of the heater 14. As described previously, the wick 28 is a bundle of flexible filaments whose end portions are disposed within the confines of the supply reservoir 22. The contents of the pre-vapor formulation supply reservoir 22 may be a pre-vapor formulation, as previously described, together with the end portions of the wick 28. The end portions of the wick 28 occupy substantial portions of the tank interior such that orientation of the e-vaping device 60 does not impact the ability of the wick 28 to draw pre-vapor formulation. Optionally, the pre-vapor formulation supply reservoir 22 may include filaments or gauze or a fibrous web to maintain distribution of pre-vapor formulation within the pre-vapor formulation supply reservoir 22.

In operation, with the e-vaping device 60 in an assembled configuration, an adult vaper may apply a negative pressure on the mouth-end insert 8. This negative pressure may cause an internal pressure drop inside e-vaping device 60 that may cause an inlet air flow to enter the e-vaping device 60 via the air inlets 44/44'. The internal pressure drop may also cause an internal pressure drop within the reusable section 72 as air is drawn through the air inlet 44a. The internal pressure drop formed in section 72 may be sensed by the puff sensor 16. The puff sensor 16 may then operate to close an electrical circuit that includes the power supply 1. In turn, electrical current is carried to the heater 14 in order to energize the heater 14. The energized heater 14 in turn heats and vaporizes pre-vapor formulation material that is drawn toward the heater 14 via the wicks 28.

As a negative pressure is being applied, the vaporized pre-vapor formulation material becomes entrained in the air flow which then passes through tube 20a of tank 70, through the mouth-end insert 8.

While the first connector element 37 has been described with reference to the e-vaping device 60, shown in FIG. 1, it should be understood that a connector element with a CC-NVM may be used in another type of e-vaping device.

Figure 7A:
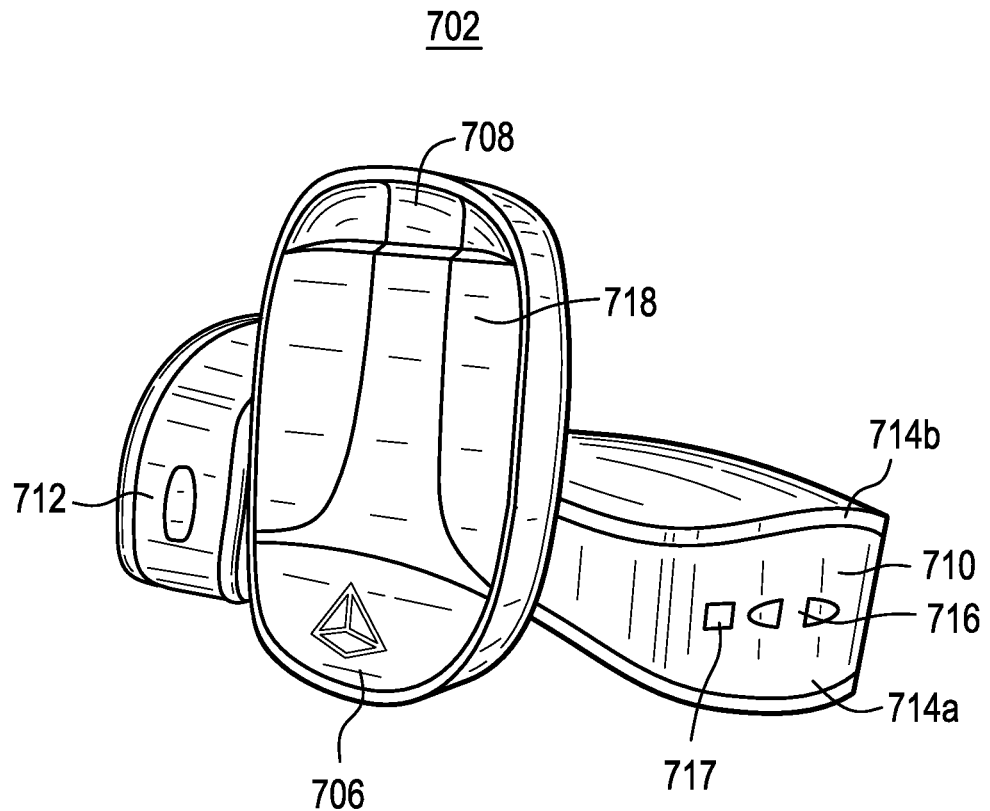
FIGS. 7A-7B illustrate a pod-type e-vaping device according to an example embodiment.
Figure 7B:
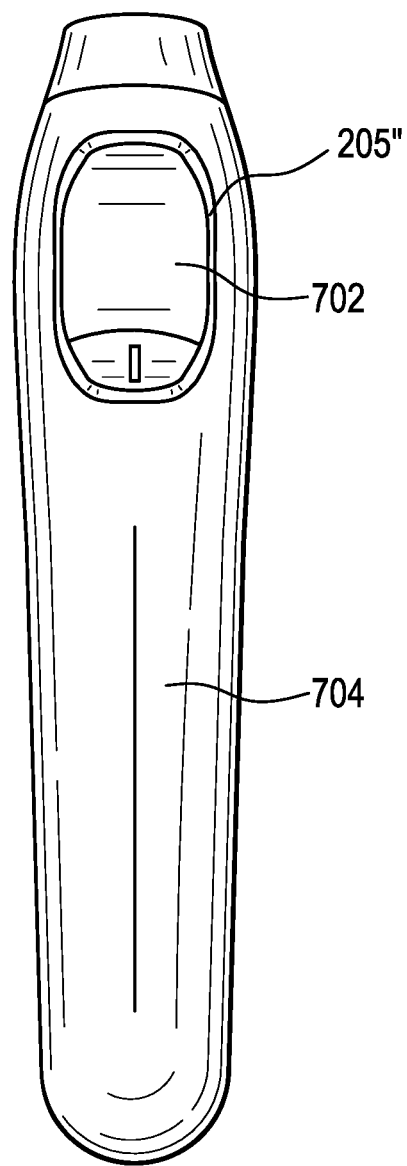

For example, FIGS. 7A-7B illustrate a pod-type e-vaping device according to an example embodiment, where a pod assembly 702 may connect to a body 704. The pod assembly 702 includes battery contacts 716 and a data connection 717 connected to a CC-NVM within the pod assembly 702. The CC-NVM within the pod assembly 702 is configured to communicate with a controller in the body 704.

Referring to FIG. 7A, each of the pod assemblies 702 includes a pod trim 710 arranged between a first cap 714a and a second cap 714b. The vapor channel 708 is aligned with the channel outlet 712 and arranged above the vaporizer 706. The pod assembly 702 is sealed to hold a pre-vapor formulation 718 therein and to preclude tampering therewith. As shown in the example embodiment of FIG. 7A, the pre-vapor formulation 718 fills to near a top of the pod assembly 702. The pre-vapor formulation compartment of the pod assembly 702 is configured to hold the pre-vapor formulation 718, and the device compartment includes the vaporizer 706. For example, the CC-NVM may be connected to a portion of the pod assembly 702 separate from the vaporizer 706 and pre-vapor formulation 718. In one example embodiment, the CC-NVM is attached to an internal surface of the trim 710. In another example embodiment, the CC-NVM is connected to a printed circuit board (PCB) in the pod assembly that is separate from the vaporizer 706 and pre-vapor formulation 718. Thus, the pod assembly 702 may be considered to have at least three sections, one with the pre-vapor, one where the vaporizer 706 resides and one containing the connector bits and the CC-NVM.

In further detail, the pod assembly 702 for an e-vapor apparatus may include a pre-vapor formulation compartment configured to hold an pre-vapor formulation 718 therein. A device compartment is in fluidic communication with the pre-vapor formulation compartment. The device compartment includes a vaporizer 706. A vapor channel 708 extends from the device compartment and traverses the pre-vapor formulation compartment.

The pod assembly 702 is configured for insertion into a dispensing body. As a result, the dimensions of the pod assembly 702 may correspond to the dimensions of the through-hole of the dispensing body. The vapor channel 708 may be between a mouthpiece and the device compartment when the pod assembly 702 is inserted into the through-hole of the dispensing body.

A connection 205" (e.g., male/female member arrangement, e.g., connection 205" shown in FIG. 7B) may be provided on at least one of the side wall of the through-hole and a side surface of the pod assembly 702. The connection 205" may be the connection shown in FIG. 3C. Thus, the CC-NVM 320 may be the CC-NVM described with reference to FIG. 7A.

The connection 205" may be configured to engage and hold the pod assembly 702 upon insertion into the through-hole of the dispensing body. In addition, the channel outlet 712 may be utilized to secure the pod assembly 702 within the through-hole of the dispensing body. For instance, the dispensing body may be provided with a retractable vapor connector that is configured to insert into the channel outlet 712 so as to secure the pod assembly 702 while also supplementing the vapor path from the channel outlet 712 to a vapor passage.

The pre-vapor formulation compartment and the CC-NVM package may be at opposite ends of the pod assembly 702. The device compartment may include a memory device. The non-volatile memory of the CC-NVM may be coded with an electronic identity to permit at least one of an authentication of the pod assembly 702 and a pairing of operating parameters specific to a type of the pod assembly 702 when the pod assembly 702 is inserted into the through-hole of the dispensing body (e.g., smart calibration). The electronic identity may help prevent counterfeiting. The operating parameters may help optimize a vaping experience without placing a burden on the adult vaper to determine preferred settings. In an example embodiment, the level of the pre-vapor formulation in the pod assembly 702 may be tracked. Additionally, the activation of the pod assembly 702 may be restricted once its intended usage life has been exceeded. Thus, the pod assembly 702 (and 302) may be regarded as a smart pod.

A side surface of the pod assembly 702 includes at least one electrical contact 716 (e.g., two contacts) for power and at least one electrical contact 717 (data connection) for data. The CC-NVM package is connected to the electrical contact 717 and one of the contacts 716. The dispensing body may be configured to perform at least one of supply power to and communicate with the pod assembly 702 via the at least one electrical contact 716. The at least one electrical contact 716 may be provided at an end of the pod assembly 702 corresponding to the device compartment. Because of its smart capability, the pod assembly 702 may communicate with dispensing body and/or another electronic device (e.g., smart phone). As a result, usage patterns and other information (e.g., puff size, flavor intensity, throat feel, puff count) may be generated, stored, transferred, and/or displayed.

As shown in FIG. 7B, an e-vapor apparatus 700 includes the pod assembly 702 (e.g., smart pod) that is inserted within a dispensing body 704.

The smart capability, connecting features, and other related aspects of the pod assembly, dispensing body, and overall e-vapor apparatus shown in FIGS. 7A-7B are additionally discussed in U.S. application Ser. No. 14/998,020 (Atty. Dkt. No. 24000-000174-US (ALCS2829)) filed on Apr. 22, 2015, entitled POD ASSEMBLY, DISPENSING BODY, AND E-VAPOR APPARATUS INCLUDING THE SAME, and U.S. application Ser. No. 14/998,040 (Atty. Dkt. No. 24000-000202-US (ALCS2855)) filed on Apr. 22, 2015, entitled E-VAPOR DEVICES INCLUDING PRE-SEALED CARTRIDGES, the entire contents of each of which are incorporated herein by reference.

FIG. 8 illustrates another example embodiment of an e-vaping device configured to utilize a connection arrangement shown in FIGS. 3B-C.

As shown in FIG. 8, an e-vaping device 800 includes a main body 805. The main body includes a mouthpiece 810, a control section 815 and a receiving section 820.

The receiving section 820 is configured to receive a replaceable cartridge 825. The replaceable cartridge includes a channel 830, a pre-vapor formulation container 835, a heater 840 and a first connector element 845. The first connector element 845 includes a CC-NVM package 850. The heater 840 heats pre-vapor formulation in the pre-vapor formulation container 835 into a vapor. The vapor is then provided to the mouthpiece 810 through the channel 830.

The control section 815 includes a second connector element 852 to connect with the first connector element 845, a controller 855 and a power supply 860. The controller 855 is configured to communicate with the CC-NVM package 850 and use the CC-NVM package 850 to authenticate the cartridge 825, as previously described with respect to FIGS. 3A-7B. If the cartridge 825 is authenticated, the controller 855 permits the power supply 860 to provide power the heater 840.

The controller 855 may be hardware, firmware, hardware executing software or any combination thereof. When the controller 18 is hardware, such existing hardware may include one or more Central Processing Units (CPUs), digital signal processors (DSPs), application-specific-integrated-circuits (ASICs), field programmable gate arrays (FPGAs) computers or the like configured as special purpose machines to perform the functions of the controller 855.

In the event where the controller 855 is a processor executing software, the controller 855 is configured as a special purpose machine to execute the software, stored in a computer readable storage medium 875, to perform the functions of the controller 855.

An adult vaper may activate the e-vaping device 800 by pressing a button 865. The button 865 may be a toggle button or a capacitive touch sensor, for example. Upon pressing the button 865, the power supply 860 provides power to the heater 840.

If the controller 855 is unable to authenticate the cartridge 825, the controller 855 may disable the button 865 and/or the power supply 860.

Moreover, the controller 855 may disable the button 865 and/or the power supply 860 if the amount of pre-vapor formulation in the pre-vapor formulation container 835 is below a threshold level, if the puff count with respect to the cartridge exceeds a threshold number or based on any other parameters associated with the cartridge 825.

While FIGS. 3B-3E illustrate a male/female connection, example embodiments are not limited thereto. For example, the connection may include a mating member that is formed on a side wall of the first connector element 37 and/or the second connector element 36 and a corresponding recess that is formed on the side surface of the pod assembly. Conversely, the mating member may be formed on the side surface of the pod assembly, while the corresponding recess may be formed on the side wall of the first connector element 37 and/or the second connector element 36. In a non-limiting embodiment, the mating member may be a rounded structure to facilitate the engagement/disengagement of the connection 205", while the recess may be a concave indentation that corresponds to the curvature of the rounded structure.

The mating member may also be spring-loaded so as to retract (via spring compression) when a pod (e.g., as shown in FIGS. 7A-7B) is being inserted into a through-hole and protract (via spring decompression) when mating member becomes aligned with the corresponding recess. The engagement of the mating member with the corresponding recess may result in an audible click, which notifies the adult vaper that the pod assembly is secured and properly positioned within the through-hole of the e-vaping device.

In another example, the connection may include a magnetic arrangement. For instance, a first magnet may be arranged in the side wall of the first connector element 37 and/or the second connector element 36, and a second magnet may be arranged in the side surface of the pod assembly. The first and/or second magnets may be exposed or hidden from view behind a layer of material.

Example embodiments having thus been described, it will be obvious that the same may be varied in many ways. Such variations are not to be regarded as a departure from the intended spirit and scope of example embodiments, d all such modifications as would be obvious to one skilled in the art are intended to be included within the scope of the following claims.

What is claimed is:

1. A cartridge for an electronic vapor (e-vapor) apparatus, comprising:
    a pre-vapor formulation compartment configured to hold a pre-vapor formulation therein;
    a first connector configured to connect the cartridge to a power section of the e-vapor apparatus, the first connector including at least one power connector, the at least one power connector including two prongs, and a wall of the first connector being spaced apart from a first prong of the two prongs to define a gap therebetween;
    a processing device configured to communicate with the power section, the processing device being disposed within the gap and in contact with (i) the wall of the first connector and (ii) the first prong of the two prongs; and
    a housing surrounding at least a portion of the first connector,
    wherein the processing device further includes
        a first pin configured to connect to the housing and provide a data communication line, and
        a second pin configured to connect to the first prong of the two prongs.

2. The cartridge of claim 1, wherein the at least one power connector is configured to connect to the power section.

3. The cartridge of claim 2, wherein
    the first connector includes a first portion and a second portion divided by an indented portion of the first connector, the indented portion defining an opening between the first portion and the second portion,
    the at least one power connector extends from the first portion to the second portion, and
    the processing device is coupled to the at least one power connector in the first portion.

4. The cartridge of claim 1, wherein the processing device is not connected to a printed circuit board (PCB).

5. The cartridge of claim 1, wherein the processing device is a cryptographic coprocessor with non-volatile memory (CC-NVM).

6. The cartridge of claim 5, wherein the CC-NVM is configured to adjust cryptographic keys based on vaping parameters.

7. An electronic vapor (e-vapor) apparatus comprising:
a first section including a controller; and
a second section including
a pre-vapor formulation compartment configured to hold a solution therein;
a first connector configured to connect the second section to the first section, the first connector including at least one power connector, the at least one power connector including two prongs, and a wall of the first connector being spaced apart from a first prong of the two prongs to define a gap therebetween;
a processing device configured to communicate with the controller, the processing device being disposed within the gap and in contact with (i) the wall of the first connector and (ii) the first prong of the two prongs; and
a housing surrounding at least a portion of the first connector,
wherein the processing device further includes
a first pin configured to connect to the housing and provide a data communication line, and
a second pin configured to connect to the first prong of the two prongs.

8. The e-vapor apparatus of claim 7, wherein the
at least one power connector is configured to connect to a power supply of the first section.

9. The e-vapor apparatus of claim 8, wherein
the first connector includes a first portion and a second portion divided by an indented portion of the first connector, the indented portion defining an opening between the first portion and the second portion,
the at least one power connector extends from the first portion to the second portion, and
the processing device is coupled to the at least one power connector in the first portion.

10. The e-vapor apparatus of claim 7, wherein the processing device is not connected to a printed circuit board (PCB).

11. The e-vapor apparatus of claim 7, wherein the processing device is a cryptographic coprocessor with non-volatile memory (CC-NVM).

12. The e-vapor apparatus of claim 11, wherein the CC-NVM is configured to adjust cryptographic keys based on vaping parameters.

13. The cartridge of claim 1, wherein
a second prong of the two prongs is spaced apart from the first prong of the two prongs to define a second gap, and the second prong of the two prongs is not in contact with the processing device.

14. The cartridge of claim 1, wherein the two prongs are configured to connect to battery contacts of the power section.

15. The e-vapor apparatus of claim 7, wherein
the first prong of the two prongs is coupled to: (i) a first side of the processing device and (ii) a second side of the processing device, and
the two prongs are configured to connect to battery contacts of the first section.

16. The e-vapor apparatus of claim 7, wherein
a second prong of the two prongs is spaced apart from the first prong of the two prongs to define a second gap, and the second prong of the two prongs is not in contact with the processing device.

* * * * *